United States Patent [19]
Partyka et al.

[11] 4,001,238
[45] Jan. 4, 1977

[54] 1,3,4-OXADIAZOLE AMIDES

[75] Inventors: Richard Anthony Partyka, Liverpool; Ronnie Ray Crenshaw, Dewitt, both of N.Y.

[73] Assignee: Bristol-Myers Company, New York, N.Y.

[22] Filed: Feb. 18, 1976

[21] Appl. No.: 658,979

[52] U.S. Cl. .............. 260/256.4 B; 260/256.4 Q; 424/251
[51] Int. Cl.$^2$ .................................. C07D 239/84
[58] Field of Search .............. 260/256.4 Q, 256.4 B

[56] References Cited
UNITED STATES PATENTS

| | | | |
|---|---|---|---|
| 3,511,836 | 5/1970 | Hess | 260/256.4 Q |
| 3,935,213 | 1/1976 | Hess | 260/256.4 Q |

*Primary Examiner*—Paul M. Coughlan, Jr.
*Attorney, Agent, or Firm*—Robert E. Havranek

[57] ABSTRACT

The 4-amino-6,7-dimethoxy-2-[4-(5-lower alkylthio-1,3,4-oxadiazole-2-carbonyl)-piperazin-1-yl]-quinazolines are potent antihypertensive drugs which have little or no α-adrenergic blocking activity.

3 Claims, No Drawings

1,3,4-OXADIAZOLE AMIDES

BACKGROUND OF THE INVENTION

1. Field of the Invention

This invention relates to 4-amino-6,7-dimethoxy-2-[4-(5-lower alkylthio-1,3,4-oxadiazole-2 carbonyl)-piperazin-1-yl]-quinazolines.

2. Description of the Prior Art

U.S. Pat. Nos. 3,511,386; 3,635,979; and 3,663,706 disclose various 4-amino-6,7-dimethoxy-2-[4-(heterocyclic-2-carbonyl)-piperazin-1-yl] quinazolines. One of these compounds, i.e., 2-[4-(2-furoyl)-piperazin-1-yl]-4-amino-6,7-dimethoxyquinazoline described in Example LXXII of these patents is a clinically useful antihypertensive agent and is marketed as such in many countries of the world under the generic name prazosin. It is well established that the antihypertensive efficacy of prazosin results from a dual mechanism of action: (i) a direct peripheral vasodilation effect on vascular smooth muscle, and (ii) a functional peripheral α-adrenergic receptor blockade, H. Adriaensen, The Practitioner, 214, 268 (1975); Mroczek, et al., Current Therapeutic Research, 16, 769 (1974); Scriabine, et al., Experientia, 24, 1150 (1968); Constantine, et al., "Hypertension: Mechanisms and Management", ed. by Onesti, Kim and Moyer; Grune and Stratton, 1973 pp. 429–44; and Zacest, Med. J. of Austral. Special Supplement, 1,4 (1975). Although initial clinical assessments on prazosin indicated an almost complete absence of side effects, recent reports have revealed severe adverse reactions of postural hypotension in some patients, Bendall, et al., Brit. Med. J., 727 (June 28, 1975); Rees, Brit. Med. J., 593 (Sept. 6, 1975); Gabriel, et al., The Lancet, 1095 (May 10, 1975); and Bloom, et al., Current Therapeutic Research, 18, 144 (1975). It is generally felt that this type of side effect results from the α-blockade component of prazosin. Indeed, it has been stated by R. Zacest in the Med. J. of Austral., Special Supplement, 1, 4 (1975) that "if the alpha adrenergic 'blocking' activity does prove to be significant with high doses it may lead to postural hypotension".

U.S. Pat. Nos. 3,669,968 and 3,769,286 cover trialkoxyquinazolines, such as those having the formula:

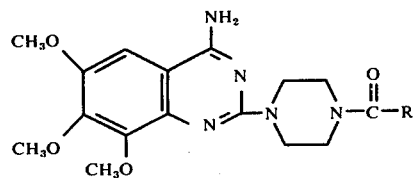

wherein R may be a number of different groups including furyl and thienyl. These patents claim to have certain advantages over the corresponding 6,7-dialkoxy compounds such as those disclosed in the patents previously discussed. Thus, it is stated that such compounds "have a more favorable pharmacological profile (e.g., they are non-adrenolytic in dogs) and possess greatly improved solubility characteristics (particularly in water) as contrasted to the corresponding 6,7-dialkoxy compounds reported in the prior art". One of the compounds disclosed in these patents is known by the generic name trimazosin and has the formula:

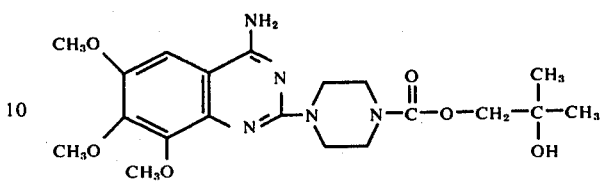

Trimazosin is reported to be active in humans as an antihypertensive agent, DeGuia, et al., Current Therapeutic Research, 15, 339 (1973); Vlachakis, et al., Current Therapeutic Research, 17, 564 (1975). However, it is a much weaker drug than prazosin, the respective clinical daily dose ranges being approximately 150 to 500 mg. for trimazosin as compared to 1.5 to 15 mg. for prazosin. Trimazosin is therefore 100-fold weaker than prazosin at the lower end of the dosage range.

U.S. Pat. Nos. 3,517,005; 3,594,480; and 3,812,127 describe certain piperazinyl quinazolines having both bronchodilator and antihypertensive activity, e.g., a compound having the formula:

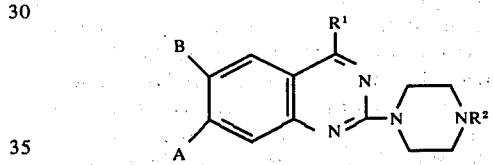

wherein A and B may each be alkoxy, etc., $R^1$ may be hydrogen or alkyl and $R^2$ may be hydrogen or a radical such as alkyl, benzoyl, etc.

U.S. Pat. No. 3,920,636 describes homopiperazino quinazolines as antihypertensive agents, e.g., the compound:

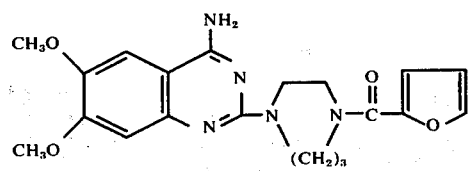

U.S. Pat. No. 3,780,040 discloses compounds useful as antihypertensive agents such as the compound:

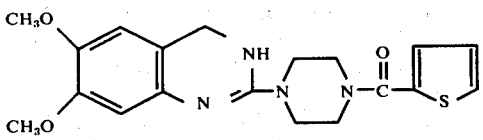

Netherlands application 72 06,067 (CA, 78, 72180s) describes a process for preparing aminoquinazolines, such as prazosin, by treating the corresponding o-aminobenzonitrile in the presence of phenyl lithium according to the following mechanism:

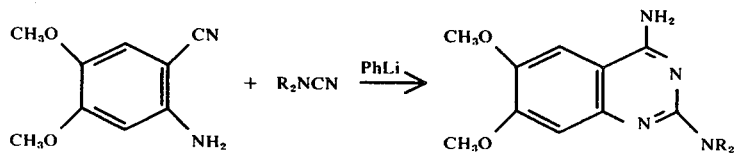

wherein R₂N may be the group 4-(2-furoyl)-1-piperazinyl.

SUMMARY OF THE INVENTION

Compounds having the formula:

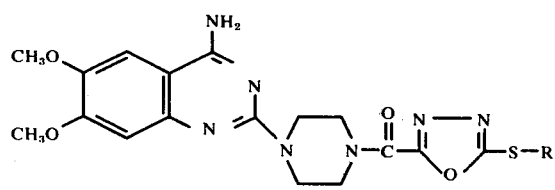

in which R is (lower)alkyl having from 1 to 6 carbon atoms and pharmaceutically acceptable acid addition salts thereof, possess antihypertensive potency comparable to prazosin but have little or none of the peripheral α-adrenergic blocking properties shown by prazosin. These compounds are potent antihypertensive agents which have little or no potential for side effect as reflected by their lack of adrenolytic activity.

The preferred compound of this invention is 4-amino-6,7-dimethoxy-2-[4-(5-methylthio-1,3,4-oxadiazole-2-carbonyl)-piperazin-1-yl]-quinazoline or the acid salts thereof.

COMPLETE DISCLOSURE

The compounds of this invention may be prepared by several different methods. The preferred method, which will be exemplified in the examples appearing hereinafter, involves the following reaction:

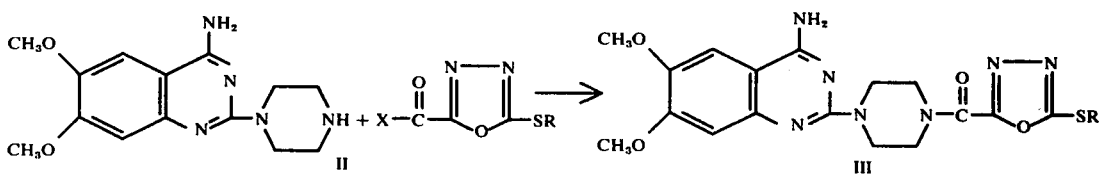

wherein R is a (lower)alkyl group of from 1 to 6 carbon atoms and X is a carbonyl activating group of the type typically used in amidation reactions, e.g., halo, azido, ethoxycarbonyloxy, 1-imidazo, etc. The preparation of compounds I and II will be described hereinafter. The reaction of compound I with compound II is preferably conducted in an inert solvent such as dioxane, chloroform, methylene chloride, glyme and the like at room temperature, with heating at reflux briefly to insure completion of the reaction.

A preferred embodiment of this invention is the compound

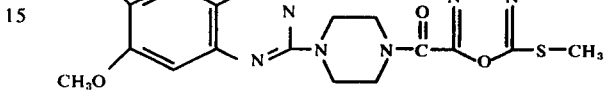

or the hydrochloride salt thereof.

The process for the preparation of the compounds of this invention is also new and novel. The preferred process for preparing compounds having the formula

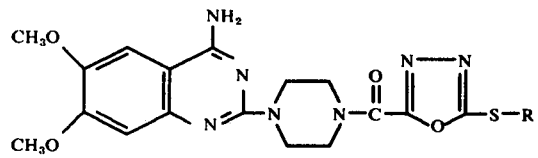

wherein R is a (lower)alkyl group comprises acylating a compound having the formula

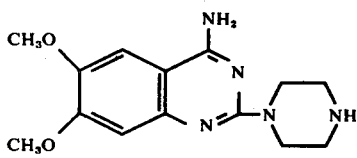

with a compound having the formula

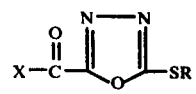

wherein R is a (lower)alkyl group and X is a carbonyl activating group. In a preferred embodiment, the reaction is conducted in the presence of an inert solvent such as dioxane, methylene chloride, glyme and the like.

The most preferred process comprises acylating a compound having the formula

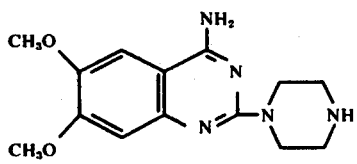

with a compound having the formula

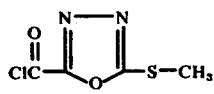

in dioxane to provide a product having the formula

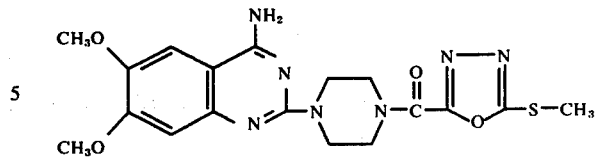

A second method which may be employed to prepare the compounds of this invention is illustrated by the following equation.

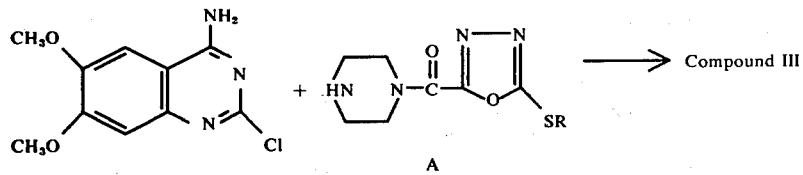

wherein R is a (lower)alkyl group.

Another method for the preparation of the compounds of this invention involves the following reaction sequence:

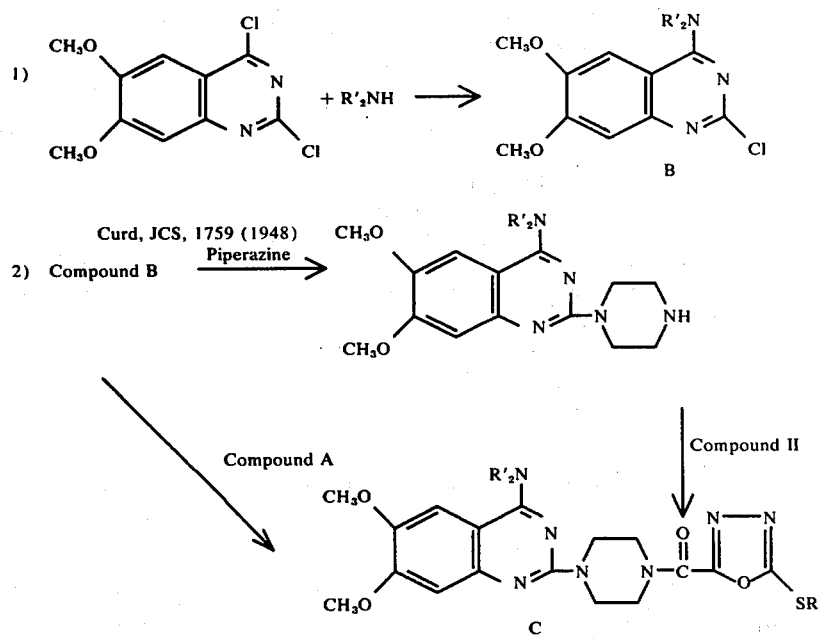

wherein $R'_2$ is a conventional amine protecting group (e.g., a t-butoxycarbonyl group) and wherein R is a (lower)alkyl group. The amine protecting group may then be removed from compound C by conventional means to provide the desired product, compound III.

Another procedure for the preparation of compounds of this invention is illustrated by the following reaction sequence:

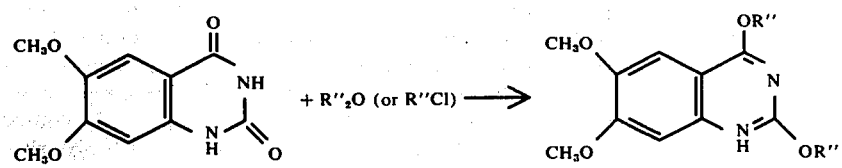

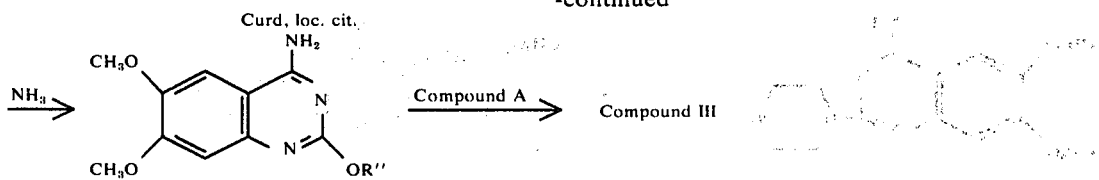

wherein R'' is a group such as F$_3$CC(O), CH$_3$SO$_2$, F$_3$CSO$_2$, aryl SO$_2$, etc.

Still another method for the preparation of compounds of this invention is illustrated in the following reaction sequence:

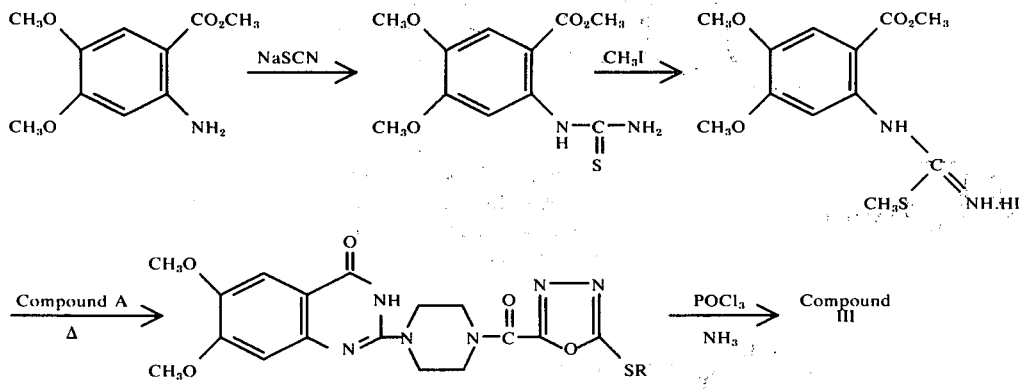

wherein R is a (lower)alkyl group.

The following experiments illustrate the preparation of intermediate compound II. Experiment A shows the reaction equation for the formation of compound II wherein R is methyl and X is Cl. Each individual step in the reaction is described.

Experiment A

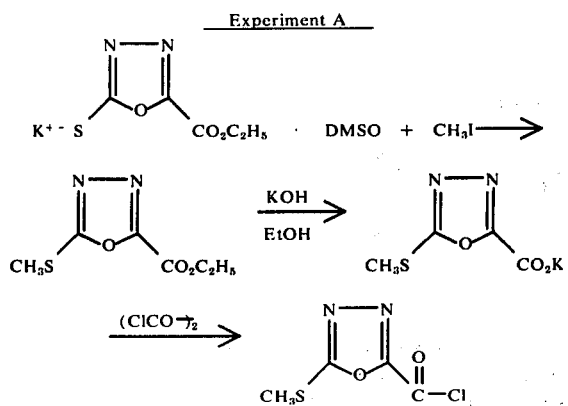

Ethyl 5-methylthio-1,3,4-oxadiazole-2-carboxylate

A mixture of ethyl-1,3,4-oxadiazole-2-thione-5-carboxylate potassium salt dimethylsulfoxide solvate (45.0 g.; 0.122 mole; D. E. Horning et al., Can. J. Chem., 50, 3079 (1972)) and methyl iodide (52.0 g., 0.366 mole) in absolute ethanol (400 ml.) was stirred at reflux for 45 minutes. The cooled reaction mixture was concentrated to a semi-solid. Water (about 600 ml.) was added, the mixture was filtered and the precipitated solid washed with water and dried to yield the title compound (15.6 g., M.P. 77°–79° C.). An additional 4.08 g., M.P. 70°–76° C. was obtained from the filtrate and water washings to provide a total yield of 19.68 g. (70%).

Potassium 5-methylthio-1,3,4-oxadiazole-2-carboxylate

A solution of ethyl 5-methylthio-1,3,4-oxadiazole-2-carboxylate (4.31 g., 0.023 mole) in absolute ethanol (50 ml.) was treated dropwise with 2.87 g. (0.023 mole) of 45 wt.% potassium hydroxide solution. The resultant white precipitate was isolated by filtration, washed with ethanol and dried to yield 3.92 g. (86%) of the title compound; M.P. 176°–177° C. with decomposition after recrystallization from ethanol.

Anal. Calcd for C$_4$H$_3$N$_2$O$_3$SK: C, 24.23; H, 1.53; N, 14.13.
Found: C, 24.33; H, 1.66; N, 14.26.

5-Methylthio-1,3,4-oxadiazole-2-carbonyl chloride

A solution of oxalyl chloride (2.57 ml., 0.03 mole) in benzene (15 ml.) was added dropwise to a refluxing suspension of potassium 5-methylthio-1,3,4-oxadiazole-5-carboxylate (3.96 g., 0.02 mole) in benzene (50 ml.). After the addition, the mixture was stirred at reflux for one hour. Filtration and evaporation left the acid chloride; distillation gave 1.86 g. (52%); B.P. 65°–69° C. at 0.05 mm. of mercury.

Experiments B, C and D describe the preparation of compounds having other (lower)alkyl groups as the R substituent on compound II.

EXPERIMENT B

Ethyl 5-ethylthio-1,3,4-oxadiazole-2-carboxylate

A mixture of ethyl 1,3,4-oxadiazole-2-thione-5-carboxylate potassium salt dimethylsulfoxide solvate (11 g., 0.03 mole) and ethyl iodide (7 g., 0.045 mole) in absolute ethanol (100 ml.) was heated at reflux for 45 minutes and then worked up as described previously in Experiment A to yield the title compound (5.59 g.).

5-Ethylthio-1,3,4-oxadiazole-2-carbonyl chloride

The title compound was prepared from the above ester analogously to the procedure described in Experiment A, B.P. 86° C. at 0.04 mm. of mercury.

EXPERIMENT C

Ethyl 5-isopropylthio-1,3,4-oxadiazole-2-carboxylate

The title compound was prepared from ethyl 1,3,4-oxadiazole-2-thione-5-carboxylate potassium salt dimethylsulfoxide solvate (11 g., 0.03 mole) and isopropyl iodide (5.6 g., 0.03 mole) analogously to the procedure described in Experiment A. The yield was 4.1 g. (63%).

5-Isopropylthio-1,3,4-oxadiazole-2-carbonyl chloride

The title compound was prepared from the above ester analogously to the procedures described under Experiment A. The yield was 2.04 g. (66%). The product had a B.P. of 70°–74° C. at 1 mm. of mercury.

EXPERIMENT D

Ethyl 5-n-propylthio-1,3,4-oxadiazole-2-carboxylate

The title compound was prepared from ethyl 1,3,4-oxadiazole-2-thione-5-carboxylate potassium salt dimethylsulfoxide solvate (10 g., 28.5 mmole) and n-propyliodide (4.17 ml., 42.8 mmole) analogously to the procedure described in Experiment A. The yield was 4.99 g. (81%). The product had a B.P. of 108°–118° C. at 0.65 mm. of mercury.

5-n-Propylthio-1,3,4-oxadiazole-2-carbonyl chloride

The title compound was prepared from the above ester analogously to the procedures described under Experiment A. The product had a B.P. of 75°–84° C. at 0.4 mm. of mercury.

The following experiment shows the preparation of compound I:

EXPERIMENT E

4-Amino-6,7-dimethoxy-2-(1-piperazinyl)quinazoline (I)

Piperazine hydrobromide (168.0 g., 1.006 mole) was added to a suspension of 4-amino-2-chloro-6,7-dimethoxyquinazoline (241.0 g., 1.006 mole) in 2-methoxyethanol (3.6 l.) and the mixture was stirred at reflux for 1.25 hours. The precipitate was separated by filtration, washed with hot 2-methoxyethanol and dried. The material then was added to a stirred solution of sodium hydroxide (81.0 g., 2.01 mole) in water (3 l.) and the mixture was heated to 75° C. The mixture then was cooled to 40° C., filtered, and the insoluble precipitate washed with water and dried. The material was triturated under refluxing absolute ethanol (6.0 l.) and the mixture was filtered. The filtrate was evaporated to dryness to yield the title compound, 180.0 g. (62%), M.P. 224°–228° C.

Compound I can exist in two polymorphic forms. In an earlier experiment similar to Experiment E with the exception that an excess of piperazine hydrobromide was used, a water soluble form (Isomorph A) of Compound I having a M.P. of 224°–228° C. was obtained. This product was recrystallized from nitromethane to give an analytical sample of Isomorph A having a M.P. of 227°–229° C.

Anal. Calcd for $C_{14}H_{19}N_5O_2$: C, 58.12; H, 6.62; N, 24.20. Found: C, 58.23; H, 6.75; N, 24.22.

A 200 mg. sample of Isomorph A was dissolved in 10 ml. of water at 20° C. The solution was heated at 60° C. for 3 minutes, then cooled to 35° C. and filtered. The precipitate (157 mg.), M.P. 228°–230° C. would not redissolve in boiling water. This product was termed Isomorph B of Compound I.

Anal. Calcd for $C_{14}H_{19}N_5O_2$: C, 58.12; H, 6.62; N, 24.20. Found: C, 57.77; H, 6.54; N, 24.05.

The infrared spectra of Isomorph A and Isomorph B of Compound I show distinct differences. The product obtained from the large scale experiment — i.e., Experiment E, is Isomorph B.

As previously discussed, compounds of this invention are valuable antihypertensive agents, possessing comparable antihypertensive potency to prazosin. However, they have little or none of the peripheral α-adrenergic blocking properties shown by prazosin. The compounds may be used in the form of the free base or in the form of pharmaceutically acceptable acid salts thereof, such as salts of sulfuric acid, hydrochloric acid, succinic acid, tartaric acid, benzoic acid, etc. The compounds may be administered orally or parenterally with oral administration being preferred. Generally, dosages will range from 0.1 to 10 mg. 3 to 4 times per day per human adult. As is usual in antihypertensive therapy, the particular optimum dosage may vary considerably depending upon the sensitivity of the patient to the drug and the severity of the hypertension.

EXAMPLES

EXAMPLE 1

4-Amino-6,7-dimethoxy-2-[4-(5-methylthio-1,3,4-oxadiazole-2-carbonyl)-piperazin-1-yl]-quinazoline hydrochloride A solution of 5-methylthio-1,3,4-oxadiazole-2-carbonyl chloride (0.601 g., 3.36 mmole) in dioxane (10 ml.) was added to a solution of 4-amino-6,7-dimethoxy-2-(1-piperazinyl)quinazoline (0.972 g., 3.36 mmole) in dioxane (100 ml.). The resultant mixture was stirred at room temperature for 65 hours, then was heated at reflux for 30 minutes. Filtration gave the title compound (1.56 g.). Recrystallization from methanol gave a product having a M.P. of 280°–285° C. with decomposition.

Anal. Calcd for $C_{18}H_{21}N_7O_4S \cdot HCl$: C, 46.20; H, 4.74; Cl, 7.58; N, 20.96; S, 6.85. Found: C, 46.34; H, 4.89; Cl, 7.59; N, 20.38; S, 6.58.

EXAMPLE 2

4-Amino-6,7-dimethoxy-2-[4-(5-ethylthio-1,3,4-oxadiazole-2-carbonyl)-piperazin-1-yl]-quinazoline hydrochloride The title compound was prepared from 5-ethylthio-1,3,4-oxadiazole-2-carbonyl chloride (0.79 g., 4.1 mmole) and 4-amino-6,7-dimethoxy-2-(1-piperazinyl)-quinazoline (1.19 g., 4.1 mmole) following the procedure described in Example 1. The product had a M.P. of 246°–248.5° C.

Anal. Calcd for $C_{19}H_{23}N_7O_4S \cdot HCl$: C, 47.34; H, 5.02; N, 20.34; S, 6.65. Found: C, 47.37; H, 4.76; N, 20.15; S, 6.71. (corrected for 4.11% $H_2O$).

EXAMPLE 3

4-Amino-6,7-dimethoxy-2-[4-(5-isopropylthio-1,3,4-oxadiazole-2-carbonyl)-piperazin-1-yl]-quinazoline hydrochloride The title compound was prepared from 5-isopropylthio-1,3,4-oxadiazole-2-carbonyl chloride (1.54 g., 7.5 mmole) and 4-amino-6,7-dimethoxy-2-(1-piperazinyl)quinazoline (2.1 g., 7.5 mmole) following the procedure of Example 1. The product had a M.P. of 260°–263° C. with decomposition.

Anal. Calcd for $C_{20}H_{25}N_7O_4S \cdot HCl$: C, 48.43; H, 5.28; N, 19.77. Found: C, 48.05; H, 5.20; N, 19.61.

EXAMPLE 4

TABLE 1

[Structure: 4-amino-6,7-dimethoxyquinazoline with 2-piperazinyl substituent, piperazine N-R]

| Compound | R | Antihypertensive Activity | | | | α-Adrenergic Receptor Blocking Effect | | |
|---|---|---|---|---|---|---|---|---|
| | | Dose mg/kg | % Blood Pressure Change | ED50 mm Hg mg/kg | Activity Ratio | In Vitro Activity Ratio | In Vivo Activity Ratio | IV LD$_{50}$ in mice mg/kg |
| Prazosin | [2-furoyl group: −C(=O)−furan] | 10<br>3<br>1 | −42<br>−29<br>−14 | 2.1 | 1.0 | 1.0 | 1.0 | 36.1 |
| BL-5111 | [5-methylthio-1,3,4-oxadiazol-2-yl carbonyl: −C(=O)−oxadiazole−SCH$_3$] | 10<br>3<br>1 | −41<br>−26<br>−19 | 2.3 | 0.91 | 0 | 0.04 | 45.7 |

4-Amino-6,7-dimethoxy-2-[4-(5-n-propylthio-1,3,4-oxadiazole-2-carbonyl)-piperazin-1-yl]-quinazoline hydrochloride The title compound was prepared from 5-n-propylthio-1,3,4-oxadiazole-2-carbonyl chloride (1.68 g., 8.16 mmole) and 4-amino-6,7-dimethoxy-2-(1-piperazinyl)quinazoline (2.36 g., 8.16 mmole) following the procedure of Example 1. The product had a M.P. of 230°–245° C. with decomposition.

Anal. Calcd for $C_{20}H_{25}N_7O_4S \cdot HCl$: C, 48.43; H, 5.25; N, 19.77. Found: C, 48.11; H, 5.35; N, 19.65.

EXAMPLE 5

4-Amino-6,7-dimethoxy-2-[4-(5-n-butylthio-1,3,4-oxadiazole-2-carbonyl)-piperazin-1-yl]-quinazoline hydrochloride The title compound was prepared from 5-n-butylthio-1,3,4-oxadiazole-2-carbonyl chloride and 4-amino-6,7-dimethoxy-2-(1-piperazinyl)quinazoline following the procedure of Example 1.

To determine the efficacy of the compounds of this invention as antihypertensive agents, tests were conducted comparing the product of Example 1 to prazosin. The results of these tests are set forth in Table 1. As shown in Table 1, the product obtained in Example 1, above (hereinafter referred to as BL-5111) is of comparable antihypertensive potency to prazosin, but has little or none of the peripheral α-adrenergic blocking properties shown by prazosin. The compounds described and claimed in this application thus represent a significant and unexpected advance in the continuing quest for potent antihypertensive drugs which have little or no potential for side effects as reflected by their lack of α-adrenergic blocking activity.

In Table 1, antihypertensive activity was determined by oral administration to spontaneous hypertensive rats, and the in vitro and in vivo α-adrenergic receptor blocking effect was determined by tests described following Table 1. In the in vitro test, the inhibition by BL-5111 of norepinephrine induced contractions of rat seminal vesicles was measured; and in the in vivo test, the inhibition by BL-5111 of norepinephrine induced pressor responses in anesthetized dogs was measured. The in vivo tests were conducted using intravenous administration, each compound being assayed in 4 dogs with 2 dose response results in each dog.

ISOLATED RAT SEMINAL VESICLE ASSAY

Dangan et al, Int. J. Neuropharmacol., 4:219 (1965) have shown that the seminal vesicle of the rat is a tissue which is notably responsive to compounds which activate α-receptors but is relatively insensitive to compounds which activate β-receptors. Lietch et al, Brit. J. Pharmacol., 9:236 (1954), have employed the isolated rat seminal vesicle in the comparative assay of α-receptor blocking drugs and the present studies were carried out using a modification of their procedure.

Male Long Evans rats weighing approximately 300 g. were sacrificed by a sharp blow on the head. Seminal vesicles were removed and transfered to a shallow dish containing modified Tyrode's solution. The vesicles were emptied of their contents by squeezing them gently with a pair of forceps. Silk thread (4–0) was attached to both ends of the vesicle and it was suspended in a 20 ml. muscle chamber containing modified oxygenated Tyrode's solution (g./liter: NaCl 8, KCl 0.2, CaCl$_2$ 0.26, NaHCO$_3$ 1, Na$_2$HPO$_4$ 0.0575, glucose 0.5 and MgCl$_2$ 0.02). The bathing fluid was maintained at 37° C. with a thermostatically controlled isolated organ tissue bath. Contractions were recorded isometrically by means of a force displacement transducer and recordings were made with a Beckman RP Dynograph. Norepinephrine (NE) was added to the muscle chamber in volumes ranging from 0.1 to 0.4 ml. with a one ml. syringe attached to a 3 inch 20 gauge needle. NE and test compounds were dissolved in deionized water.

NE dose response curves were obtained alone and in the presence of test compounds. NE was allowed to remain in contact with the strip until a maximal contraction was obtained. The strip was then washed with the perfusion fluid for 15–30 seconds and the preparation was allowed to return to base line before a subsequent dose of NE was given. Increasing amounts of NE were injected into the bath in the same manner until a complete dose response was obtained.

The seminal vesicles used to obtain the control NE dose response were discarded and new preparations were placed in the tissue bath for evaluation of the test compound. The test compound was added directly to the perfusion fluid (10 nanograms/ml.) and the strips were allowed to remain in contact with the bathing media for at least 10 minutes before the NE dose response was determined.

ED50 values for NE were obtained by regression analysis as described by Finney, Probit. Analysis, 2d Ed., Cambridge (1964). A minimum of 4 strips and at least 4 doses were employed to calculate the regression lines. The ED50 value is defined as the concentration of NE which produces a contraction equal to 50% of the maximal contraction.

The ratio of the α-adrenergic blocking activity of BL-5111 relative to that of prazosin was calculated as follows:

$$\% \text{ Change from NE} = \frac{\text{ED50 NE + Drug} - \text{ED50 NE Alone}}{\text{ED50 NE Alone}} \times 100$$

The value obtained for BL-5111 was then expressed as a ratio of the value obtained for prazosin.

$$\text{Activity Ratio} = \frac{\% \text{ Change for NE} - \text{BL-5111}}{\% \text{ Change from NE Prazosin}}$$

The results obtained with NE, prazosin and BL-5111 are summarized in Table II.

Table II

| | | Effect of Prazosin and BL-5111 on NE Response in Isolated Rat Seminal Vesicles | | |
|---|---|---|---|---|
| Treatment | No. of Strips | NE ED50 with 95% Conf. Limits (μg/ml) | Percent Change From Control | Activity Ratio Relative to Prazosin |
| Control | 32 | 0.89 (0.84–0.94) | — | — |
| Prazosin, 10 nano/ml. | 8 | 6.03 (5.30–6.81) | 578 | 1.0 |
| BL-5111 10 nano/ml. | 7 | 0.93 (0.80–1.08) | 4.5 | 0.008 |

These data indicate rather clearly that at a concentration of 10 nanograms/ml., prazosin caused nearly a six fold decrease in the sensitivity of isolated rat seminal vesicles to the stimulant activity of NE while BL-5111 was essentially inactive in this respect. It was concluded that BL-5111 possesses less than one percent of the α-adrenergic blocking activity of prazosin.

ANESTHETIZED DOG ASSAY FOR
α-ADRENERGIC BLOCKING AGENTS

Nash, C. B., Pharmacological Research Communications, 4:423, (1969) and Maxwell, R. A., Drill's Pharmacology in Medicine, (1971) p. 683 have shown that in anesthetized dogs α-adrenergic blocking agents antagonize the blood pressure elevating effects of intravenous norepinephrine. Thus, blood pressure responses to norepinephrine (NE) in anesthetized dogs was used as a comparative assay for α-adrenergic receptor blocking properties of drugs.

Experiments were done on mongrel dogs anesthetized with sodium pentobarbital, 30 mg./kg. iv. The left femoral artery was cannulated to record aortic blood pressure and a femoral vein was cannulated for administration of drugs. All animals underwent a bilateral vagotomy. A norepinephrine dose-response curve was obtained by administering increasing doses of iv. norepinephrine (0.01 – 1 μg/kg). The test drug (prazosin, BL-5111) was then administered iv. at 3 mg/kg. Approximately 30 minutes later a dose-response curve was again established for iv. norepinephrine (0.01–10 μg/kg). The dose of norepinephrine (with 95% confidence limits) that increased blood pressure by 50 mm of Hg was obtained from dose-response curve analysis before and after prazosin and BL-5111. The ratio of the α-adrenergic blocking activity of BL-5111 relative to that of prazosin was obtained as follows:

$$\text{Activity Ratio} = \frac{\frac{\text{ED50 mm Hg}}{\text{BL-5111}} - \frac{\text{ED50 mm Hg}}{\text{NE}}}{\frac{\text{ED50 mm Hg}}{\text{Prazosin}} - \frac{\text{ED50 mm Hg}}{\text{NE}}}$$

The results obtained with norepinephrine, prazosin and BL-5111 are summarized in Table III. The results indicate that BL-5111 was approximately 30 times less active than prazosin in causing α-adrenergic blockade at 3 mg/kg iv.

Table III

Effect of Prazosin and BL-5111 on the Blood Pressure Response to Intravenous Norepinephrine Table III

| | | Effect of Prazosin and BL-5111 on the Blood Pressure Response to Intravenous Norepinephrine | |
|---|---|---|---|
| Treatment | N | NE ED50 mm Hg w/95% Conf. Limits | Activity Ratio Relative to Prazosin |
| Control | 20 | 0.23 (0.19–0.28) | — |
| Prazosin, 3 mg/kg | 4 | 6.90 (4.80–10.7) | 1.00 |
| BL-5111 | 4 | 0.47 (0.40–0.55) | 0.036 |

We claim:
1. A compound having the formula:

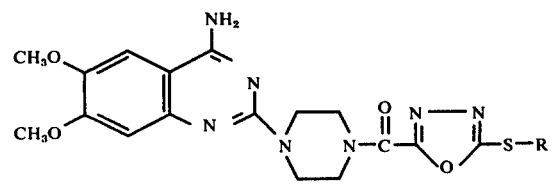

in which R is (lower)alkyl of 1 to 6 carbon atoms; or a pharmaceutically acceptable acid addition salt thereof.
2. A compound of claim 1 in which R is (lower)alkyl of 1 to 4 carbon atoms.
3. The compound having the formula:

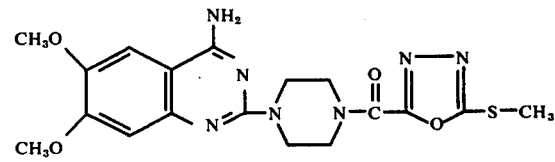

or the hydrochloride salt thereof.

* * * * *